Figure 1:
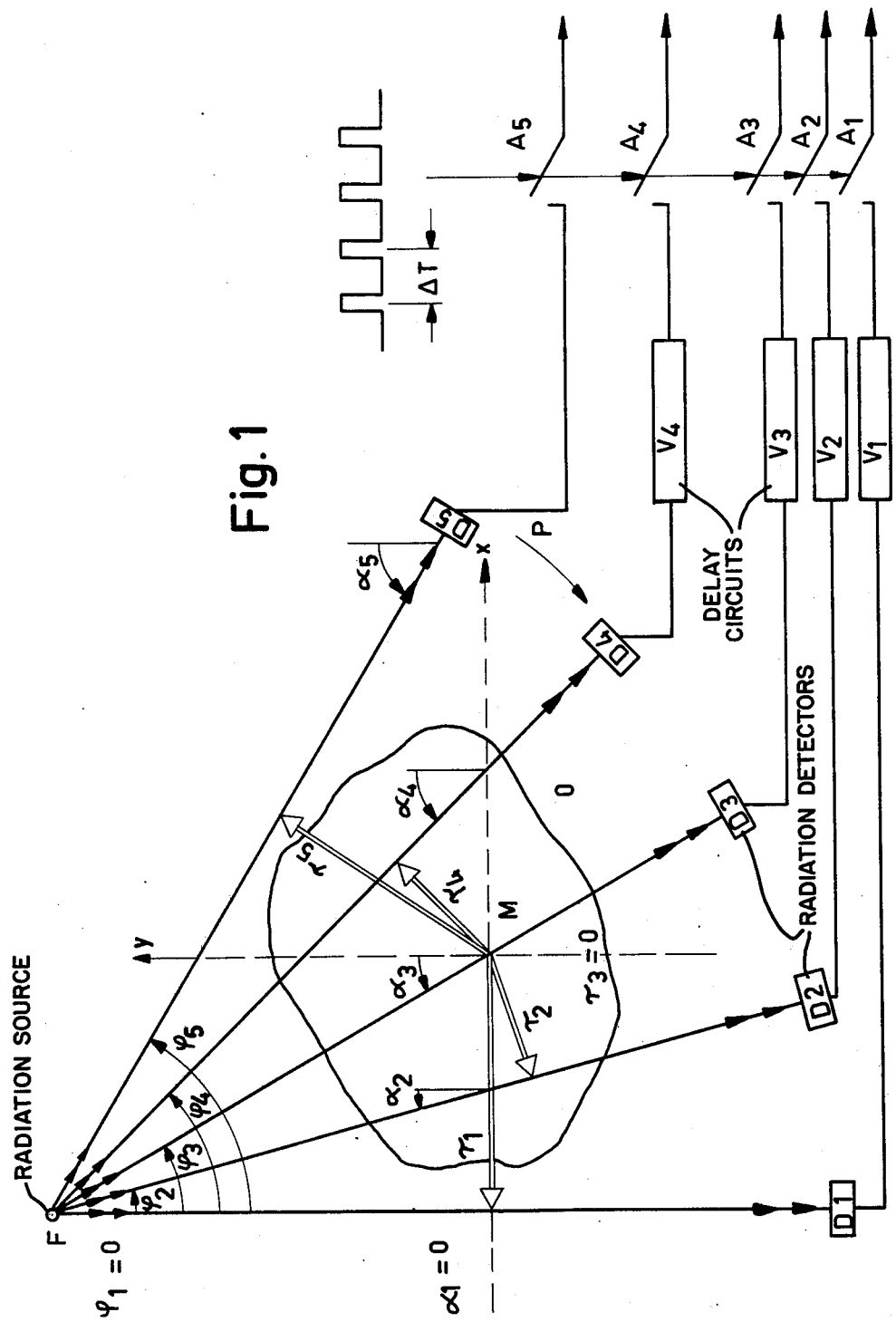

United States Patent [19]

Kowalski

[11] 4,075,490
[45] Feb. 21, 1978

[54] DEVICE FOR MEASURING RADIATION ABSORPTION IN A LAYER OF A BODY

[75] Inventor: Günter Kowalski, Hamburg, Germany

[73] Assignee: U.S. Philips Corporation, New York, N.Y.

[21] Appl. No.: 675,175

[22] Filed: Apr. 8, 1976

[30] Foreign Application Priority Data

Apr. 19, 1975 Germany .............................. 2517440

[51] Int. Cl.² ............................................ G01N 23/00
[52] U.S. Cl. ................................................. 250/445 T
[58] Field of Search .................... 250/445 T, 336, 415

[56] References Cited

U.S. PATENT DOCUMENTS

| | | | |
|---|---|---|---|
| 3,772,512 | 11/1973 | Laney | 250/366 |
| 3,881,110 | 4/1975 | Hounsfield et al. | 250/445 T |
| 3,946,234 | 3/1976 | Hounsfield | 250/445 T |
| 3,973,128 | 8/1976 | Lemay | 250/445 T |

*Primary Examiner*—Bruce C. Anderson
*Attorney, Agent, or Firm*—Frank R. Trifari; Jack E. Haken

[57] ABSTRACT

A device for measuring the absorption of radiation in a layer of a body, utilizing a radiator emitting a fanned radiation beam which passes through the body and which is measured by a number of adjacently arranged detectors. The radiator/detector system is rotated with respect to the body during the measurement. Integral measuring values of mutually intersecting sets of parallel strips are used for calculating the absorption. To this end, the device comprises means for sampling signals supplied by the detectors at different instants and/or means for effecting the sampling after different signal delay times.

13 Claims, 3 Drawing Figures

DEVICE FOR MEASURING RADIATION ABSORPTION IN A LAYER OF A BODY

The invention relates to a device for measuring radiation absorption in a layer of a body, utilizing a radiator which emits a fanned radiation beam which passes through the body and which is measured by a number of adjacently arranged detectors, the radiator/detector system being rotated with respect to the body, during the measurement, integral measuring values of mutually intersecting sets of parallel strips being used for calculating the absorption.

It is known (German Offenlegungsschrift No. 1,941,433) to measure the spacial distribution of radiation absorption in a layer or "slice" of a body by measuring the absorption of the radiation by the body in a large number of directions and in a large number of locations by means of a radiator and a detector which is arranged behind the body and which is oriented towards the radiator. During a measurement of this kind the radiator/detector system is displaced perpendicularly with respect to the radiation direction, the absorption being measured in a large number of directly adjoining strips. Subsequently, the radiator/detector system is rotated through a given angle, after which the operation is repeated etc. The absorption in individual points of a layer of the body can be calculated from the measuring values thus obtained which are each time a measure for the integral of the absorption along the straight connecting line between radiator and detector.

Even though the calculation in an apparatus of this kind is comparatively accurate, the time required for obtaining the necessary measuring values amounts to a few minutes, so that only bodies or parts of the body can be examined which can be maintained absolutely immobile, because otherwise blurring due to motion is unavoidable.

It is known (for example, from German Offenlegungsschrift No. 2,426,343) to perform the necessary measurements substantially faster by means of a large number of detectors which are arranged behind the object to be examined and which cover a fanned radiation beam emitted by a radiator, because a large number of measuring values can thus be simultaneously obtained. The measuring values are then a measure for the integral of the absorption along straight lines to strips which are not parallel with respect to each other but which intersect at one point (at the area of the radiator). The calculation of the absorption in separate points of the layer to be examined, executed on the basis of the measuring values thus obtained, is comparatively inaccurate, because the algorithms known thus far for calculating the absorption are based on the fact that the radiation passes through the object to be examined along parallel extending straight lines or strips.

In order to enable a calculation by means of the known devices (German Offenlegungsschrift No. 1,941,433) comprising only one detector, without prolongation of the time required for the measurement, it has been proposed (German Patent Application No. P 25 11 231.6) to measure, by interpolating, the integral values of the absorption along mutually intersecting sets of parallel extending straight lines on the basis of measuring values obtained by a plurality of detectors. These interpolations are not very accurate on the one hand, while on the other hand a substantial period of time for calculation and also a large number of storage positions are required.

The invention has for its object to provide a device of the kind set forth in which integral values of the absorption along mutually intersecting sets of parallel extending strips can be comparatively simply obtained. To this end, the device in accordance with the invention is characterized in that means are provided for sampling signals supplied by the detectors at different instants and/or means for effecting the sampling after different signal delay times.

Embodiments of the device in accordance with the invention will be described in detail hereinafter with reference to the drawing.

Figure 2:
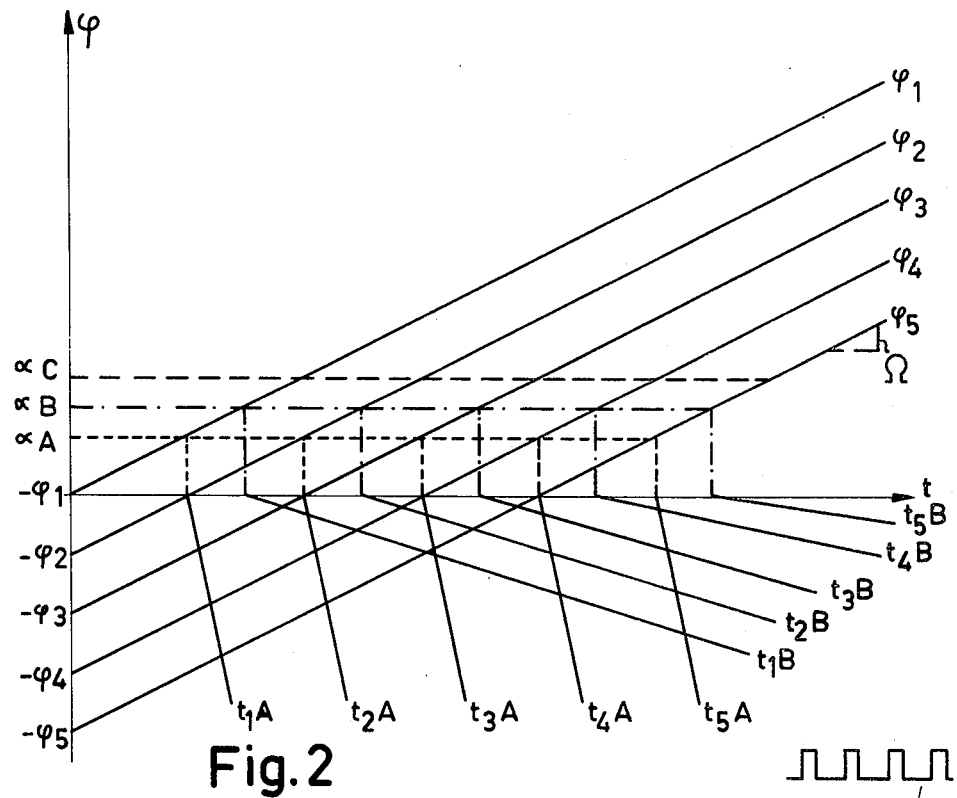
Figure 3:
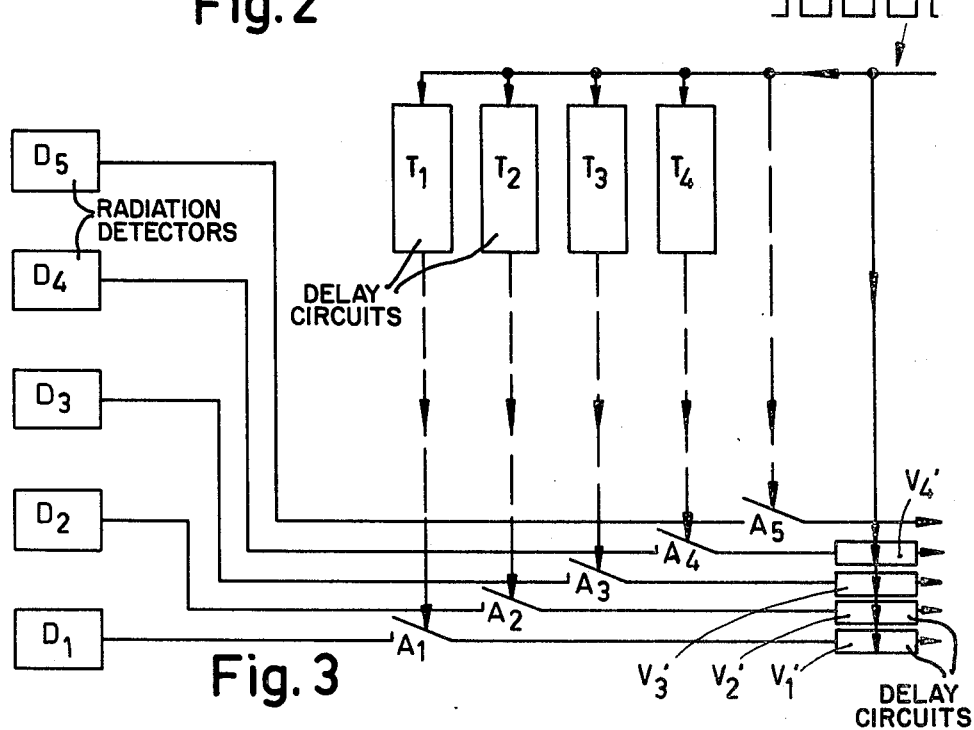

FIG. 1 is a diagrammatic representation of a first embodiment in accordance with the invention, which also illustrates the geometrical relationships, FIG. 2 shows the variation in time of the angular position of the straight connecting line between the radiator and the individual detectors, and FIG. 3 shows a further embodiment of the device in accordance with the invention.

FIG. 1 shows a radiation source F and a group of the detectors $D_1$ to $D_5$ (only five detectors are used for the purpose of illustration), which cover, behind the object O, a fanned radiation beam emitted by the radiation source. The radiation source and the group of detectors rotate together about a centre M which is preferably situated approximately in the centre of an object O. The drawing shows the geometry at the instant $t = 0$. The angles between a straight connecting line $F - D_1$ and one of the other straight connecting lines $F-D_2 \ldots F-D_5$ are denoted by $\phi 2 \ldots \phi 5$; they are constant and dictated by the construction; $\phi_1$ is always equal to 0. For the sake of simplicity, straight connecting lines are assumed between the radiator and the centre of the detectors. Actually, each time a narrow radiation beam is involved, whose opening angle is determined by the width of a detector. In practice, the detectors are adjacently arranged, so that the total radiation field can be covered.

The angles of rotation of the individual straight connection lines with respect to a fixed but arbitrary reference system $x$, $y$ are denoted by $\alpha_1 \ldots \alpha_5$. When the system rotates, these angles of rotation change at a common angular velocity $\Omega = d\alpha/dt$.

The individual beams are further defined by their distance $r_1 \ldots r_5$ from the centre of the said reference system $x$, $y$. These distances are also constant and dictated by the construction.

FIG. 2 shows the variation of the angles of rotation in the time for the individual detectors. Because all angles change at the same angular velocity (assumed to be constant for the time being), parallel extending straight lines arise which have been shifted through the angles $\phi_1 \ldots \phi_5$ between the straight connecting lines $F-D_1 \ldots F-D_5$ with respect to each other. In order to obtain the measuring values for all detectors at a predetermined angle $\theta_A$, the detector signals must be sampled at the associated instants $t_1^A \ldots t_5^A$, the time differences being defined by $$\Delta t_{mn} = t_m - t_n = \frac{\phi_m - \phi_n}{\Omega} \quad (m, n = 1 \ldots 5) \quad (1)$$

Measuring values thus obtained correspond to the integral values of the absorption along parallel extending straight lines which are situated at a distance $r_1 \ldots r_5$ from the centre O. In order to obtain the integral values of a further parallel extending set which intersects the former set at an angle $\theta_A - \theta_B$, the measuring values at the angle of rotation $\alpha_B$ must be determined. In order to obtain this value, the measuring values, that is to say the output signals of the detectors $D_1 \ldots D_5$, are sampled at instants which have been shifted by the time difference $(\alpha_A - \alpha_B)/\Omega$ with respect to the sampling instants $t_1^A \ldots t_5^A$. The time differences between the sampling instants of each time a set of measuring data then remain constant. Therefore, the device shown in FIG. 1 enables the processing of the output signals of the detectors so that each time the integral values of the absorption of the radiation along mutually intersecting sets of parallel extending strips are obtained.

To this end, behind each detector a delay member $V_1 \ldots V_4$ is connected; only the output signal of the detector $D_5$ need not be delayed, if it is assumed that the radiator/detector system rotates in the direction of the arrow P. The delays introduced by the delay members $V_1 \ldots V_4$ differ and are proportioned so that they correspond to the time required by the system for making the straight connecting line between the radiator F and the detector $D_5$ assume the same angular position as the straight connecting line between the radiator F and one of the other detectors $D_1 \ldots D_4$. The required delay time is calculated in accordance with the equation (1). For example, the delay time $\Delta t_{53}$ of the delay member $V_3$ connected behind the detector $D_3$ then follows from the equation $\Delta t_{53} = (\phi_5 - \phi_3)/\Omega$. If these conditions are satisfied, the output of the delay members $V_1 \ldots V_4$ and the output of $D_5$ carry measuring values which represent the integral values of the absorption along parallel extending straight lines (at different distances from the centre O).

A sampling member $A_1 \ldots A_5$ is each time connected behind the delay members $V_1 \ldots V_4$ and the detector D5. The sampling members $A_1 \ldots A_5$ simultaneously sample the signal applied thereto, so that on the outputs of the sampling members $A_1 \ldots A_5$ each time a set of measuring values is available which correspond to the integral values of the absorption along a set of parallel extending strips. All sampling members are controlled by a pulse from a central clock having a pulse duration.

$$\Delta T = \frac{\Delta \alpha}{\Omega} = \frac{\alpha_B - \alpha_A}{\Omega} = \frac{\alpha_C - \alpha_B}{\Omega} \text{ etc.} \quad (2)$$

The clock pulse duration $\Delta T$ thus always corresponds to the time required by the radiator/detector system for a rotation through the angle $\alpha_B - \alpha_A$, $\alpha_B$ and $\alpha_A$ being each time the angles at which the adjacently arranged parallel extending sets intersect each other.

The radiator is preferably continuously switched on during the entire measurement. The signal applied to the sampling devices $A_1 \ldots A_5$ is then filtered by a low-pass filter, as described in the previous German Patent Application No. P 25 03 789.

The delay members $V_1 \ldots V_4$ can in principle be connected behind the sampling members $A_1 \ldots A_4$. However, this implies that a delay member must simultaneously delay a plurality of sampling signals if the delay time exceeds the clock pulse duration, which is generally the case because the angle between two adjacently situated sets of parallel extending strips is smaller, for example, than the angle $\phi_5$ between F—$D_1$ and F—$D_5$.

The device shown in FIG. 1 has the drawback that a measuring error occurs if the angular velocity is not constant, and the delay times are not suitably readjusted. The readjustment of the delay time of continuously delayed analog signals, however, is very difficult from a technical point of view.

FIG. 3 shows a solution to this problem. This solution is based on the fact that the total delay is divided into an integer multiple of the clock pulse duration $\Delta T$ and a remainder which corresponds to a fraction of $\Delta T$. The delay by an integer multiple ($N_1 \ldots N_5$) of the clock pulse duration $\Delta T$ can be controlled by the clock, for example, by means of an analog or digital shift register. When use is made of a digital shift register, an analog-to-digital converter must be included in front of each shift register. This large number of analog-to-digital converters can be replaced by a single, fast analog-to-digital converter if the conversion is effected in time multiplex. In this case the sampling unit must be followed by an analog member which briefly holds the analog sampling value, (for example, a sample-and-hold member).

In FIG. 3 a sampling member $A_1 \ldots A_5$ is connected behind each detector $D_1 \ldots D_5$, each of the output signals of the members $A_1 \ldots A_4$ being delayed by a clock-controlled delay circuit $V_1' \ldots V_4'$. The remainder of the delay is achieved in that the clock signal for actuating the sampling members $A_1 \ldots A_4$ is delayed by delay members $T_1 \ldots T_4$ by the time difference $$N_n \Delta T - \Delta t_{s_n} (n = 1 \ldots 5) \quad (3)$$

A postponement of the sampling instant means an apparent reduction of the signal delay. Therefore, the delay of the signal in the delay circuits $V_1' \ldots V_4'$ must be larger than the desired delay, that is to say $$N_n > \Delta t_{s_n}/\Delta T = (\phi_5 - \phi_n)/\Delta \alpha > N_n - 1 \quad (4)$$

The clock signals are coupled to the motion of the radiator/detector system, that is to say each time when the radiator/detector system has been rotated through a given angle (for example $\alpha_A - \alpha_B$), a clock pulse appears. Fluctuations in the rotary velocity of the radiator/detector system can still be observed, but the error caused thereby is substantially smaller than in the embodiment shown in FIG. 1. The effect of fluctuations in rotary velocity is smaller as the delay time of a delay number (for example, $T_4$) is smaller with respect to that of the clock-controlled delay circuit $V_4'$ connected behind the sampling device. Moreover, the delay time can be readjusted by means of simple means, because in this case the delay of a digital signal is concerned. In the case of strongly fluctuating angular velocities, the additional shifting of the sampling instant by less than one clock pulse duration can also be correctly effected by signals relating to the various positions of the rotating radiator/detector system.

The equation (4) shows that it is advantageous for the angular differences, for example $\phi_3 - \phi_2$, to correspond to an integer multiple of the desired variation of the angle of rotation $\Delta \alpha$. This is because then $\Delta t_{s_n} = N_n \Delta T$, i.e. the total delay is realized in the clock-controlled delay circuits $V_1' \ldots V_4'$, so that the delay members $T_1 \ldots T_4$ can be dispensed with. If it is furthermore assumed that all detectors must have the same measuring area and must be directly adjacently situated for economical reasons, the detectors must be arranged on a circle segment, the radiator being situated in the centre of this cicle. However, if $\Delta\alpha$ is an integer multiple of the difference angle $\phi_m - \phi_{m-1} (m = 5 \ldots 2)$, groups of sampling members can be actuated by the same delayed clock pulse, because they always have to be delayed only by integer clock pulse durations.

For the calculation of the absorption in individual points of the layer it is of essential importance that the distances between the parallel extending straight lines or strips, along which the absorption was measured, are equal. This means (FIG. 1) that, for example, $r_5 - r_4 = r_4 - r_3$ ($r_3 = 0$). Assuming that all detectors have the same measuring areas and are adjacent, this condition is satisfied if the detectors are arranged on a segment of a circle, on the periphery of which the radiation source is situated. If the reconstruction of the image takes place in a computer which stores the measuring values or the integral values obtained therefrom by the introduction of a delay and which has random access to these values, the clock-controlled delay circuits ($V_1' \ldots V_4'$) are not necessary. They can be replaced by a correspondingly modified addressing of the storage positions, because all measuring values which would be introduced into these clock-controlled delay circuits would also arrive in the computer, be it in a different sequence.

What is claimed is:

1. In apparatus for measuring radiation absorption in a planar layer of a body of the type including: radiator and detector means which function to simultaneously measure absorption values along a plurality of intersecting straightlines in said plane and to simultaneously produce a plurality of detector signals representative thereof; and means for sequentially rotating said radiator and detector means through a large number of discrete angular displacements about said body; the angles between said lines and between said angular displacements being chosen so that at each of said angular displacements the orientation of one or more of said lines is parallel to the orientation of corresponding other of said lines at one or more prior angular displacements; the improvement comprising:

delay means for delaying said detector signals representative of values along said corresponding other lines with respect to said detector signals representative of values along said one or more lines so that sets of signals representative of values along sets of parallel lines are simultaneously produced; and switch means for simultaneously sampling said sets of signals.

2. The apparatus of claim 1 wherein said delay means include a plurality of delay circuits each connected to receive one of said detector signals at an input and to supply a delayed equivalent of said detector signal to said switch means, said delay circuits having mutually different delay times.

3. The apparatus of claim 2, wherein said delay means comprise analog signal delay devices.

4. In an apparatus for measuring radiation absorption in a layer of a body, wherein a radiator is provided for emitting a fan-shaped beam to pass through the body, a plurality of detectors are arranged adjacent one another to receive radiation from said radiator, thereby forming a radiator-detector system, means are provided for rotating the radiator-detector system relative to the body, and measuring means are connected to the detectors to provide sets of information corresponding to radiation passing at common angular displacements with respect to said body; the improvement wherein:

said measuring means comprises separate series circuits of switch means connected to receive the outputs of said detectors and delay means connected to receive outputs of said switch means, said delay means having delay times that are a function of the angular velocity of said radiator-detector system, and the operation of said switch means being synchronized with said angular velocity; and including a source of clock pulses synchronized with the angular velocity of said radiator-detector system; and means for controlling the delay of said delay means in response to said clock pulses; whereby the output of said series circuits at a given time correspond to the absorption of radiation that has passed at a common angular displacement through said body.

5. The apparatus of claim 4, wherein said delay means have delay times corresponding to integral multiples of the clock pulse duration of said clock pulses.

6. The apparatus of claim 5, further comprising means responsive to said clock pulses for operating said switch means with delays that are smaller than or equal to one clock pulse duration of said clock pulses, said clock pulse durations corresponding to the time required for said radiator-detector system to rotate through an angle corresponding to the angular displacement of radiation received from said radiator by two adjacent detectors.

7. The apparatus of claim 6, wherein said clock pulse duration is synchronized with the angular velocity of said radiator-detector system.

8. The apparatus of claim 7, wherein said switch means are responsive to the positioning of said radiator-detector system at discrete locations, for determining sampling instants.

9. The apparatus of claim 4, comprising delay members responsive to the angular velocity of said radiator-detector system for controlling said switch means.

10. The apparatus of claim 4, wherein said delay means comprise computer means and programming means for said computer means connected to employ sampled values for imaging.

11. The apparatus of claim 4, wherein said delay means comprise shift registers.

12. In an apparatus for measuring radiation absorption in a layer of a body, wherein a radiator is provided for emitting a fan-shaped beam to pass through the body, a plurality of detectors are arranged adjacent one another to receive radiation from the radiator, to form a radiator-detector system, means are provided for rotating the radiator-detector system relative to the body, measuring means are connected to the detectors to provide sets of information corresponding to radiation passing at common angular displacements with respect to said body, and a source of clock pulses is provided synchronized with the angular velocity of said radiator-detector system; the improvement comprising delay means coupled to said detectors for delaying signals from said detectors by times that are multiples of the clock pulse duration of said clock pulses, and further comprising means for sampling said detectors to apply signals therefrom to said delay means at intervals that are less than or equal to clock pulse durations.

13. The apparatus of claim 12, wherein said delay means comprises a common delay element, and means time multiplexing the outputs of said detectors to said delay element.

* * * * *